United States Patent [19]
Das et al.

[11] Patent Number: 4,513,103
[45] Date of Patent: Apr. 23, 1985

[54] 7-OXABICYCLOHEPTANE ETHERS USEFUL IN THE TREATMENT OF THROMBOLYTIC DISEASE

[75] Inventors: Jagabandhu Das, Plainsboro; Martin F. Haslanger, Lambertville, both of N.J.

[73] Assignee: E. R. Squibb & Sons, Inc., Princeton, N.J.

[21] Appl. No.: 544,300

[22] Filed: Oct. 21, 1983

[51] Int. Cl.$^3$ .................. A61K 31/34; C07D 307/00
[52] U.S. Cl. ................................. 514/469; 549/463
[58] Field of Search ..................... 549/463; 424/285

[56] References Cited
U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,218,378 | 8/1980 | Bundy | 549/417 |
| 4,220,594 | 9/1980 | Sprague | 549/459 |
| 4,228,180 | 10/1980 | Sprague | 424/285 |
| 4,254,044 | 3/1981 | Sprague | 549/463 |

FOREIGN PATENT DOCUMENTS 0043292 8/1982 European Pat. Off. .
2039909 8/1980 United Kingdom .

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane ethers of prostaglandin analogs are provided having the structural formula

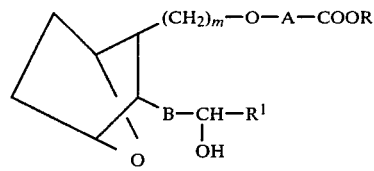

and including all stereoisomers thereof.

The compounds are cardiovascular agents useful, for example, in the treatment of thrombolytic disease.

15 Claims, No Drawings

7-OXABICYCLOHEPTANE ETHERS USEFUL IN THE TREATMENT OF THROMBOLYTIC DISEASE

DESCRIPTION OF THE INVENTION

The present invention relates to 7-oxabicycloheptane ethers which are cardiovascular agents useful, for example, in the treatment of thrombolytic disease. These compounds have the structural formula

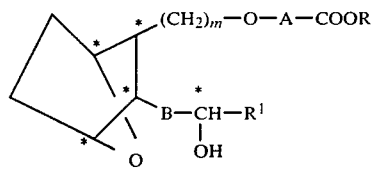

and including all stereoisomers thereof, wherein m is 1 to 4; A is $(CH_2)_n$ or $-(CH_2)_{n'}-CH=CH-$; n is 1 to 8; n' is 1 or 2; R is H, lower alkyl or alkali metal; B is $-(CH_2)_2-$ or $-CH=CH-$; and $R^1$ is lower alkyl, aryl, arylalkyl, cycloalkyl or cycloalkylalkyl.

Thus, some of the compounds within the scope of the present invention may have the following structures:

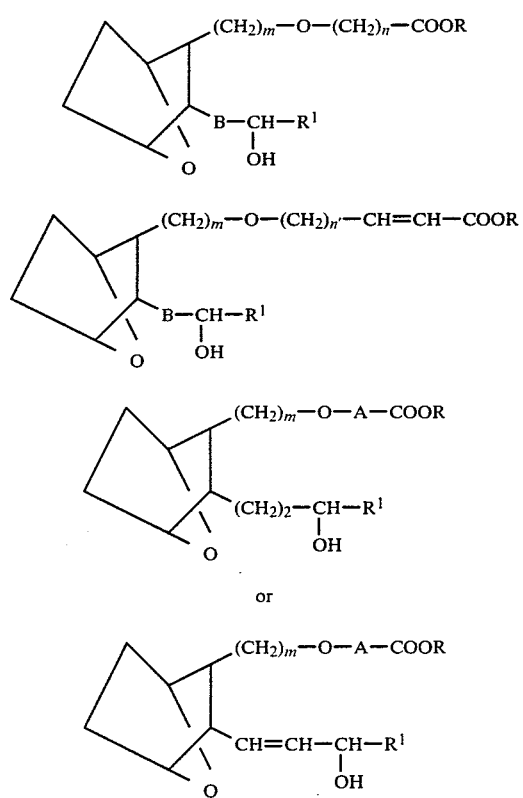

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar", as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The term "cycloalkylalkyl" as used herein refers to cycloalkyl groups as defined above linked to an alkyl group as defined above.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The terms "$(CH_2)_m$" and "$(CH_2)_n$" include straight or branched chain radicals having from 1 to 4 carbons in the normal chain in the case of "$(CH_2)_m$" and 1 to 8 carbons in the normal chain in the case of "$(CH_2)_n$", and may contain one or more lower alkyl substituents. Examples of $(CH_2)_m$ and $(CH_2)_n$ groups include $CH_2$, $CH_2CH_2$, $(CH_2)_3$, $(CH_2)_4$, $(CH_2)_5$, $(CH_2)_6$, $(CH_2)_7$,

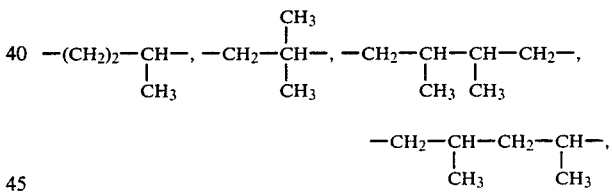

and the like.

Preferred are those compounds of formula I wherein A is $-CH=CH-$ or $-(CH_2)_2-$, m is 1 or 2, B is $-CH=CH-$ or $-(CH_2)_2$, R is hydrogen and $R^1$ is lower alkyl, phenyl or benzyl.

The various compounds of the invention may be prepared as outlined below.

The 7-oxabicycloheptane ether compounds of formula I of the invention wherein $(CH_2)_m$ is $(CH_2)_2$ or $(CH_2)_3$ and A is $(CH_2)_n$ and B is $(CH_2)_2$ may be prepared starting with the cyanoalcohol II

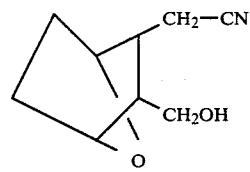

which is subjected to a benzylation wherein compound II is reacted with a base such as NaH, $NaOCH_3$, KH, KOt—C$_4$H$_9$ and the like in the presence of an inert solvent, such as dimethylformamide, dimethoxyethane or tetrahydrofuran to form the mono benzylether compound III

III

Compound III is reduced with diisobutyl aluminum hydride in the presence of an inert solvent, such as tetrahydrofuran, toluene or methylene chloride, to form the aldehyde IV

IV which may then be reduced by reaction with lithium aluminum hydride to form the alcohol V

V

Compound V is then used to prepare the final products wherein (CH$_2$)$_m$ is (CH$_2$)$_2$ as will be described hereinafter.

The 7-oxabicycloheptane ether compounds of formula I of the invention wherein (CH$_2$)$_m$ is CH$_2$ and A is —(CH$_2$)$_n$—, that is,

IA' may be prepared by subjecting the diol VI

VI to a benzylation wherein compound VI is reacted with a base such as NaH, NaOCH$_3$, KH, KOt—C$_4$H$_9$ and the like and a benzyl halide such as benzylbromide in the presence of an inert solvent such as dimethylformamide, dimethoxyethane, tetrahydrofuran or benzene to form the monobenzylether VII

VII which is used to prepare compounds of formula I wherein (CH$_2$)$_m$ is CH$_2$ as described hereinafter.

Compound V or VII herein referred to as compounds V-VII, that is

V-VII (wherein m is 2 where compound V is used and m is 1 where compound VII is used)

is subjected to O-alkylation wherein it is reacted with a base such as KOH or NaOH and a silyl compound of the structure $$\text{MesylO—(CH}_2\text{)}_n\text{—O—Si} \begin{matrix} \text{t-C}_4\text{H}_9 \\ \text{—CH}_3 \\ \text{CH}_3 \end{matrix} \quad A$$

in the presence of an aromatic solvent such as xylene, toluene or mesitylene to form the silyl compound VIII

VIII (m is 2 if V is used as the starting material or m is 1 if VII is used as the starting material)

which is desilylated by reacting same with tetra-n-butyl ammonium fluoride in the presence of an inert solvent such as tetrahydrofuran, or 40% aqueous hydrofluoric acid in tetrahydrofuran to form the alcohol IX

IX (wherein m is 2 or 1)

The alcohol IX is then made to undergo a Jones oxidation by reacting IX with chromium trioxide or other oxidizing agent such as pyridinium dichromate, in the presence of acetone or dimethylformamide to form the acid X

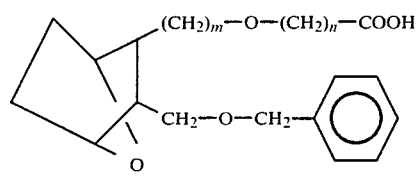

(where m is 2 or 1)
which is then subjected to esterification by reacting acid X with diazomethane or other esterifying agent of the structure RCHN$_2$ (where R is an alkyl group) to form the ester

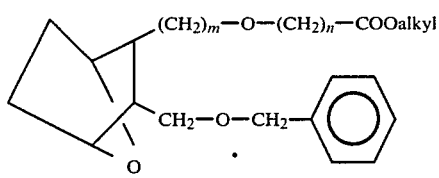

(wherein m is 2 or 1)
Ester XI is then subjected to hydrogenolysis by reacting ester XI with hydrogen in the presence of a catalyst such as palladium on carbon, platinum oxide and the like to form the alcohol XII

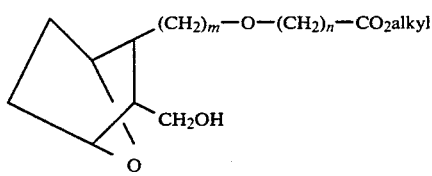

(wherein m is 2 or 1)
The alcohol XII is used to prepare aldehyde

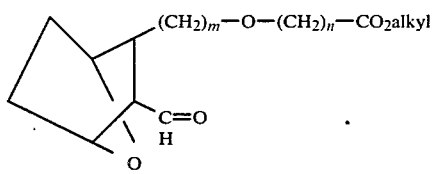

by carrying out a Collins oxidation wherein alcohol XII is reacted with CrO$_3$ in the presence of an organic base such as pyridine, in dichloromethane or with pyridinium chloro chromate in a solvent such as methylene chloride. The aldehyde XIII is then made to undergo a phosphonate reaction by reacting same with phosphonate XIV

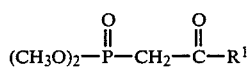

in the presence of a base such as NaH, KH, NaOCH$_3$, KOt—C$_4$H$_9$ and the like and an organic solvent such as dimethoxyethane, methylene chloride, toluene or ether to form enone compound XV

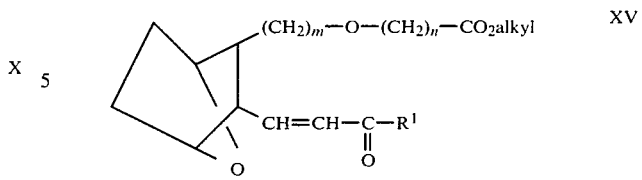

Upon reducing the enone compound XV by reaction with NaBH$_4$ in the presence of CeCl$_3$ and an alcohol solvent such as methanol, the alcohol XVI is formed

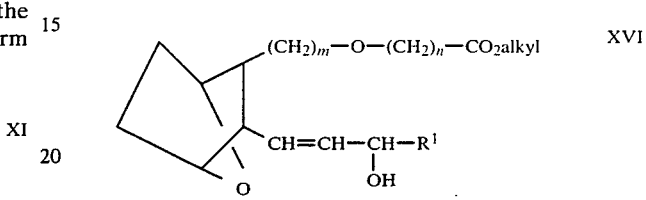

The alcohol XVI may then be hydrolyzed by reaction with a base such as LiOH, KOH or NaOH to form the corresponding alkali metal salt which is neutralized with an acid such as HCl or oxalic acid to form acid XVII

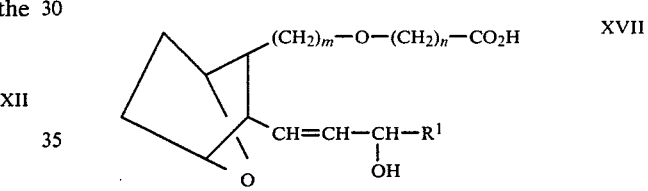

Compounds of formula I wherein m is 3 may be prepared by tosylating alcohol V with tosyl chloride in the presence of a base such as pyridine to form the tosylate XVIII

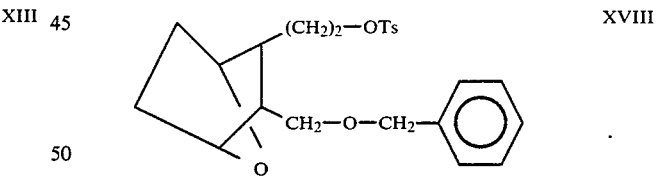

which is then reacted with an alkali metal cyanide such as sodium cyanide in the presence of an inert solvent such as dimethylsulfoxide to form nitrile XIX

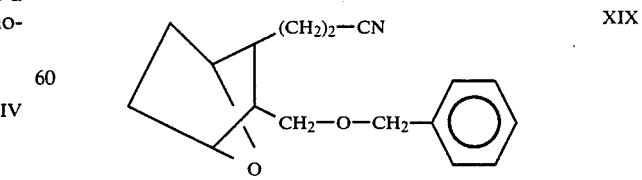

The nitrile XIX is then reduced by reaction with diisobutyl aluminum hydride in the presence of an inert solvent such as toluene to form the aldehyde XX

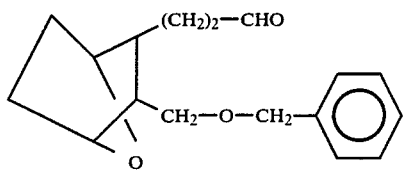
XX

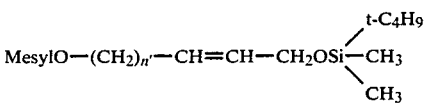
A'

(wherein $n^1$ is 1 or 2)
in the presence of an aromatic solvent such as xylene, toluene or mesitylene, to form the silyl compound

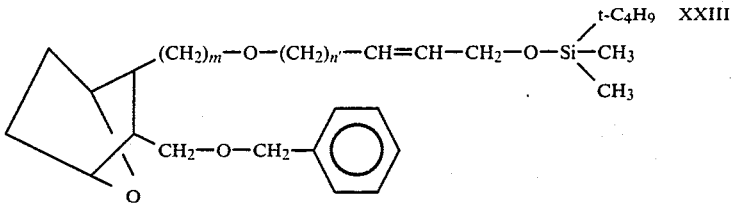
XXIII which itself is reduced by reaction with lithium aluminum hydride to form the alcohol XXI

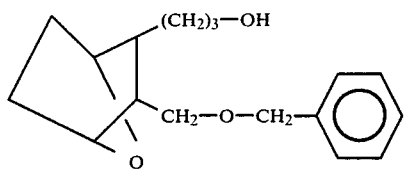
XXI

The alcohol XXI may be used in place of compound V and subjected to O-alkylation, desilylation, Jones oxidation, esterification, hydrogenolysis, Collins oxidation, phosphonate reaction, reduction and hydrolysis, as described above to form compounds of formula I wherein $(CH_2)_m$ is $(CH_2)_3$, A is $(CH_2)_n$ and B is —CH=CH—.

Compounds of formula I wherein $(CH_2)_m$ is $(CH_2)_4$ may be prepared as described above with respect to the preparation of compounds wherein $(CH_2)_m$ is $(CH_2)_3$ except that alcohol XXI is used as the starting material instead of alcohol V.

Compounds of the invention wherein A is —CH=CH—, that is, compounds of IF

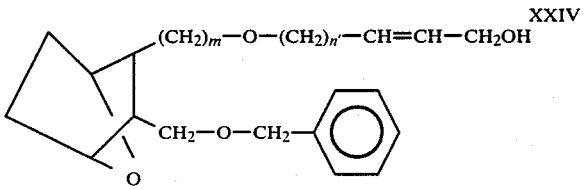
IF may be prepared by subjecting the alcohol XXII which covers alcohol VII, V, or XXI (as well as the alcohol where m is 4),

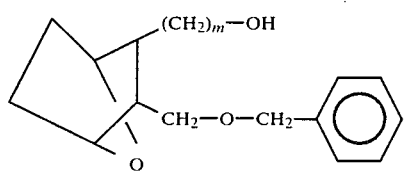
XXII to O-alkylation wherein XXII is reacted with a base such as KOH, NaOH and a silyl compound Compound XXIII is desilylated by reacting same with tetra-n-butyl ammonium fluoride in the presence of an inert solvent such as tetrahydrofuran, or with 40% aqueous hydrofluoric acid in tetrahydrofuran to form the alcohol XXIV

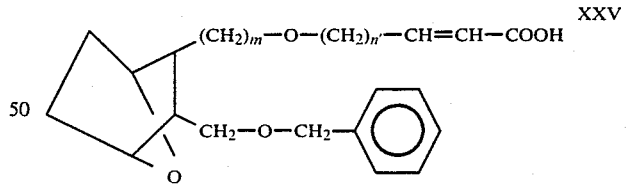
XXIV which is then subjected to a Jones oxidation as described hereinbefore with respect to alcohol IX to form the acid XXV

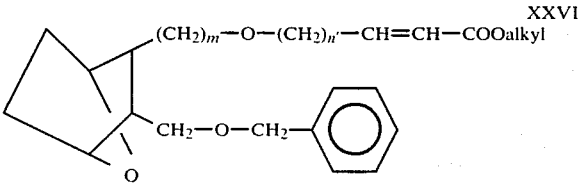
XXV which is esterified as described hereinbefore with respect to acid X to form the ester XXVI

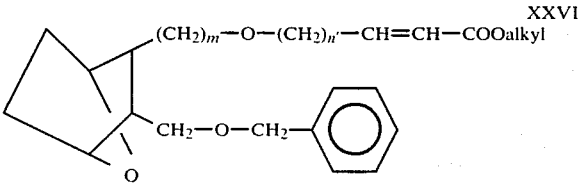
XXVI

Ester XXVI is then subjected to hydrogenolysis as described with respect to ester XI to form the alcohol XXVII

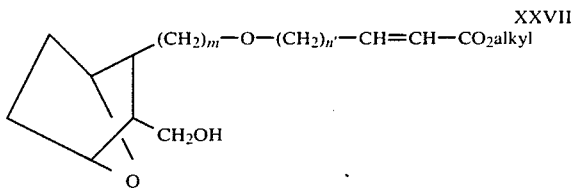

XXVII and the alcohol XXVII is converted to the corresponding aldehyde XXVIII via a Collins oxidation reaction as described with respect to alcohol XIII

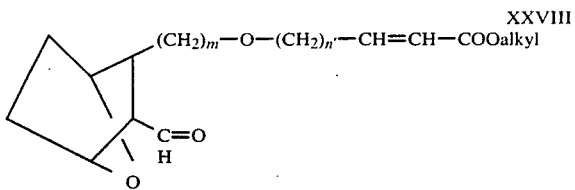

XXVIII

The aldehyde XXVIII is then reacted with phosphonate XIV as described hereinbefore with respect to aldehyde XIII to form enone XXIX

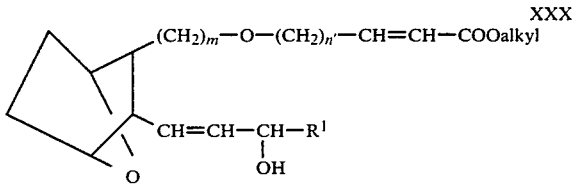

XXIX

Reduction of enone XXIX is effected as described with respect to enone XV to form alcohol XXX

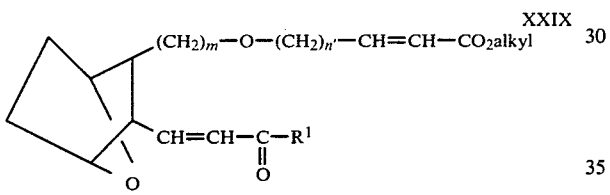

XXX

The alcohol XXX is hydrolyzed by reaction with an alkali metal hydroxide such as sodium hydroxide, potassium hydroxide or lithium hydroxide to form the corresponding alkali metal salt and which is then neutralized with an acid such as HCl or oxalic acid to the corresponding acid XXXI

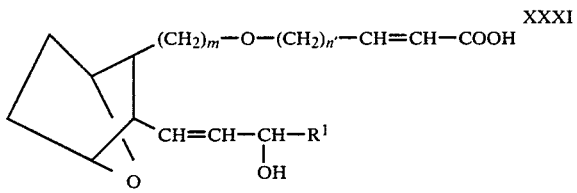

XXXI

To prepare compounds of formula I wherein A is $(CH_2)_n$ and B is $-(CH_2)_2-$, that is

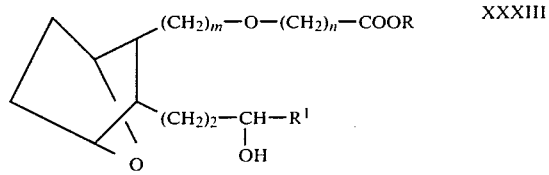

XXXIII compounds of the structure

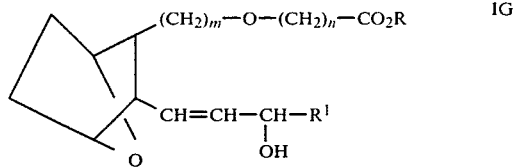

IG may be catalytically reduced by reacting same with hydrogen in the presence of a palladium on carbon catalyst to form XXXIV

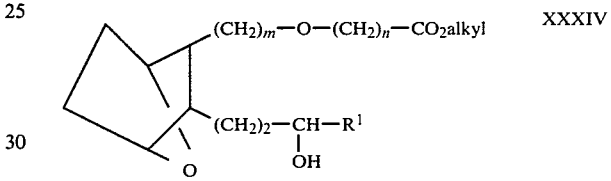

XXXIV

Compound XXXIV is then treated with an alkali metal hydroxide such as lithium hydroxide, sodium hydroxide or potassium hydroxide to form the corresponding alkali metal followed by neutralization with an acid such as dilute HCl or oxallic acid to form the corresponding acid.

The starting cyano alcohol II, that is

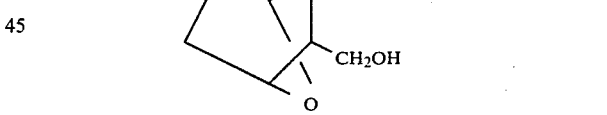

II may be prepared as follows.

The mesoanhydride

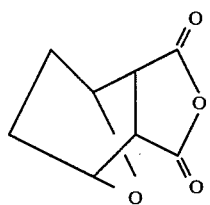

is reduced by reacting same with a reducing agent such as lithium aluminum hydride, diisobutylaluminum hydride in the presence of an inert solvent such as tetrahydrofuran or ether to form the diol VI (which may be used as the starting material for compounds wherein m is 1)

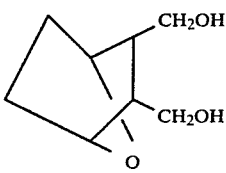

VI which is subjected to a chloroformylation reaction by reacting the diol with phosgene in the presence of an inert solvent such as tetrahydrofuran, toluene, benzene or methylene chloride or a mixture thereof to form chloroformate XXXVI

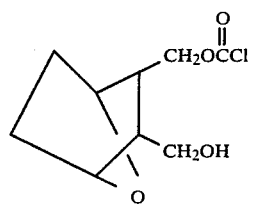

XXXVI

Chloroformate XXXVI is made to undergo cyclic-carbonate formation by reacting XXXVI with pyridine in the presence of dichloromethane to form the cyclic-carbonate XXXVII

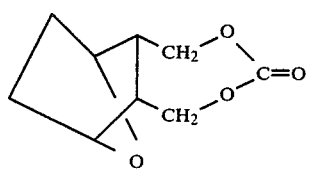

XXVII which undergoes alcoholysis by reaction with an alkanol such as isopropanol to form alcohol XXVIII

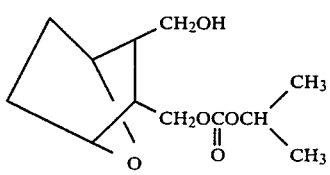

XXXVIII

Upon reacting XXXVIII with tosyl chloride in the presence of a base such as pyridine, dimethylaminopyridine, the tosylate XXXIX is formed

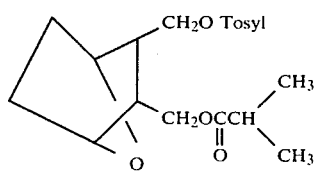

XXXIX

The tosylate XXXIX is then reacted with sodium cyanide or potassium cyanide in the presence of an inert solvent such as dimethyl sulfoxide to form the cyanide XL

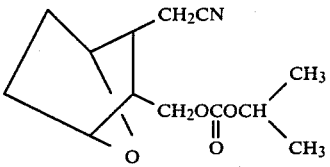

XL which may then be hydrolyzed by reaction with a basic salt such as potassium carbonate or sodium carbonate in the presence of methanol to form the starting material II.

The compounds of this invention have five centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

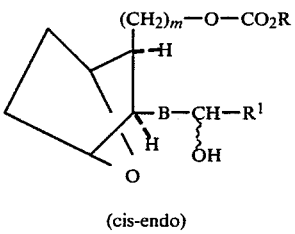

IH (cis-endo)

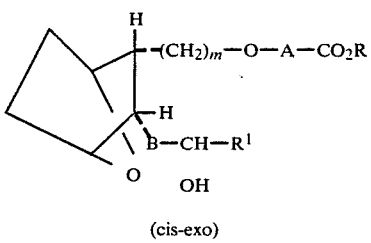

II (cis-exo)

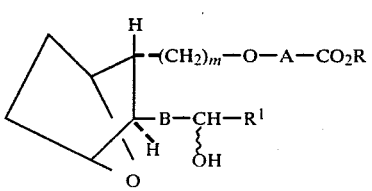

IJ (trans)

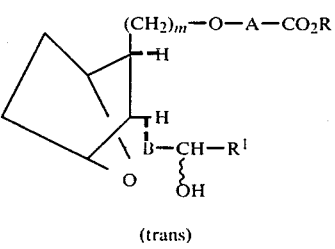

IK (trans)

The wavy ( ) line in the above formulae indicates that the hydroxy group in each of the compounds of formulae Ih-Ik is either R($\beta$) or S($\alpha$).

The nucleus in each of the compounds of the invention is depicted as

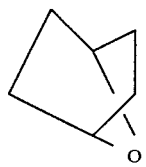

for matter of convenience; it will also be appreciated that the nucleus in the compounds of the invention may be depicted as

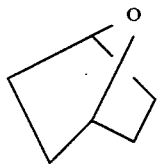

The compounds of this invention are cardiovascular agents useful as platelet aggregation inhibitors, such as arachidonic acid-induced platelet aggregation, e.g., for treatment of thrombolytic disease, such as coronary or cerebral thromboses. In addition, the compounds of the invention are useful in inhibiting bronchoconstriction such as associated with asthma. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of this invention may also be administered topically to treat peripheral vascular diseases and as such may be formulated as a cream or ointment.

The following Examples represent preferred embodiments of the invention.

EXAMPLE 1

[1$\alpha$,2$\beta$,3$\beta$(1E,3R),4$\alpha$]-5-[[3-(3-Hydroxy-4,4-dimethyl-1-octenyl)-7-oxabicyclo[2.2.1]hept-2-yl]methoxy]pentanoic acid, methyl ester

A.
(1$\alpha$,2$\beta$,3$\beta$,4$\alpha$)-Cis-exo-7-oxabicyclo[2.2.1]heptane-2,3-dimethanol To a suspension of 11.4 g lithium aluminum hydride (300 mmole, 1.6 eq) in 400 ml of dry THF at 0° C. was added dropwise a solution of 32 g cis-exo 7-oxabicyclo[2.2.1]heptane-2,3-dicarboxylic anhydride (190 mmole) in 400 ml of dry THF over a period of 1 hour. The reaction mixture was stirred at 25° C. for 18 hours, cooled to 0° C. and quenched by slow addition of a saturated $Na_2SO_4$ solution, and filtered. The solid was washed with three 100 ml portions of $CH_2Cl_2$. The combined organic layer was dried over $MgSO_4$ and concentrated to give 32 g of title diol as a colorless solid.

B.
(1$\alpha$,2$\beta$,3$\beta$,4$\alpha$)-Cis-exo-2-hydroxymethyl-3-benzyloxymethyl-7-oxabicyclo[2.2.1]heptane To a suspension of 3.08 g of sodium hydride (70 mmole, 1.1 eq., 50% oil dispersion), washed with ether, in 100 ml of dry DMF was added with stirring at 0° C. a solution of 10.0 g title A diol (64 mmole) in 30 ml of DMF over a period of 15 minutes. The mixture was stirred for 30 minutes at 0° C., 20 minutes at 25° C., cooled to 0° C. then 12.0 g of benzyl bromide (70 mmole, 1.1 eq) was added dropwise. After stirring at 25° C. for 2 hours, the reaction was quenched with an aqueous ammonium chloride solution, extracted with ether, dried over anhydrous $MgSO_4$ and concentrated.

Purification was done on a silica gel column, eluting with 10–20% ethyl acetate in hexane to give 11.8 g of the title monobenzylether.

C.
(1$\alpha$,2$\beta$,3$\beta$,4$\alpha$)-5-[[3-Benzoyloxymethyl-7-oxabicyclo[2.2.1]hept-2-yl]methoxy]pentanol, t-butyldimethylsilyl ether To a mixture of 6.73 g powdered potassium hydroxide (121 mmole, 10 eq.) in 20 ml of dry xylene was added a solution of 3.0 g of title B alcohol (12.1 mmole) in 10 ml of xylene. The mixture was heated to reflux and 15 ml of xylene was distilled off.

To the cooled remaining solution was added a solution of 6.18 g of 5-tert-butyldimethylsilyloxy n-pentyl mesylate in 10 ml of xylene. The resulting mixture was refluxed for 1 hour, cooled to 25° C. and diluted with 300 ml of ether. The ethereal solution was washed with two 50 ml portions of water, dried over anhydrous $MgSO_4$ and concentrated.

The residue was purified on a silica gel column, eluting with 20% ether in hexane to give 4.0 g of title compound as a yellow oil.

D.
(1$\alpha$,2$\beta$,3$\beta$,4$\alpha$)-5-[[3-Benzyloxymethyl-7-oxabicyclo[2.2.1]hept-2-yl]methoxy]pentanol To 536.5 mg of title C compound (1.19 mmole) in 2 ml of THF at 0° C. was added 755.4 mg of tetra-n-butylammonium fluoride. The mixture was stirred at 0° C. for 2 hours and at 25° C. for 1 hour, then diluted with 50 ml of ether. The ethereal solution was washed with two 10 ml portions of $H_2O$, 10 ml of brine, dried over anhydrous $MgSO_4$ and concentrated to give crude title alcohol as an oil. This was used without further purification.

E.
(1α,2β,3β,4α)-5-[[3-Benzyloxymethyl-7-oxabicyclo[2.2.1]hept-2-yl]methoxy]pentanoic acid, and

F.
(1α,2β,3β,4α)-5-[[3-Benzyloxymethyl-7-oxabicyclo[2.2.1]hept-2-yl]methoxy]pentanoic acid, methyl ester To crude title D alcohol in 10 ml of acetone at 0° C. was added dropwise a solution of 2.67M Jones reagent until the reaction mixture remained orange. The mixture was stirred for an additional 30 minutes at 0° C. then quenched with isopropanol and diluted with 200 ml of ether. Anhydrous sodium acetate along with anhydrous magnesium sulfate were added. The mixture was stirred for 15 minutes at 25° C. and filtered through a bed of florosil. The filtrate was concentrated and the residue was treated with 100 ml of saturated NaHCO₃ solution and extracted with two 50 ml portions of ether. The aqueous layer was acidified with concentrated HCl, saturated with solid NaCl and extracted with five 50 ml portions of $CH_2Cl_2$, dried over anhydrous $MgSO_4$ and concentrated to give 260 mg of title E acid, as an oil.

The above acid, dissolved in 10 ml of ether, was treated with an ethereal solution of diazomethane to give 260 mg of title F ester.

G.
(1α,2β,3β,4α)-5-[[3-Hydroxymethyl-7-oxabicyclo[2.2.1]hept-2-yl]methoxy]pentanoic acid, methyl ester A mixture of 260 ml title F ester (0.71 mmole) and 130 mg of 10% palladium over carbon in 5 ml of ethylacetate was shaken in a Parr bottle under 40 lbs of hyrogen pressure, at 25° C. for 18 hours. The reaction mix was filtered through a bed of Celite and the filtrate was concentratred to give 200 mg of title G alcohol as an oil.

H.
(1α,2β,3β,4α)-5-[[3-Formyl-7-oxabicyclo[2.2.1]hept-2-yl]methoxy]pentanoic acid, methyl ester To 1 ml of pyridine (7 mmole, 10 eq.) in 15 ml of dry $CH_2Cl_2$ at 25° C. was added 700 mg of chromium trioxide (7 mmole, 10 eq.). The mixture was stirred for 1 hour at 25° C. 1 g of Celite along with a solution of 200 mg of title G alcohol (0.7 mmole) in 5 ml of $CH_2Cl_2$ was added. After stirring for 30 minutes at 25° C., the reaction mixture was diluted with 100 ml of ether and filtered through a bed of florosil, and concentrated to yield 140 mg of crude title H aldehyde as an oil.

I.
[1α,2β,3β(1E),4α]-5-[[3-(3-Oxo-4,4-dimethyl-1-octenyl)-7-oxabicyclo[2.2.1]hept-2-yl]methoxy]pentanoic acid, methyl ester To a slurry of 27.4 mg of sodium hydride (0.57 mmole, 1.1 eq., 50% dispersion in mineral oil) in 5 ml of DME was added at 0° C. 200 mg of 2-oxo-3,3-dimethyl-heptyldimethylphosphonate (0.78 mmole, 1.5 eq.). The mixture was stirred for 1 hour at 25° C., cooled to 0° C. and a solution of 140 mg title H aldehyde (0.5 mmole) in 5 ml of DME added. The reaction mixture was stirred for 4 hours at 25° C. then quenched with glacial acetic acid and concentrated. The residue was diluted with 30 ml of ether and washed with two 10 ml portions of saturated NaHCO₃, 10 ml H₂O, dried over anhydrous MgSO₄ and concentrated to give the title compound as an oil: 330 mg. This was used without purification.

J.
[1α,2β,3β(1E,3R),4α]-5-[[3-(3-Hydroxy-4,4-dimethyl-1-octenyl)-7-oxabicyclo[2.2.1]hept-2-yl]methoxy]pentanoic acid, methyl ester To 330 mg of crude title I enone (ca. 0.7 mmole) in 3 ml of dry methanol at 25° C. was added 257 mg of cerium trichloride (0.7 mmole, 1 eq.). The mixture was stirred at 25° C. for 10 minutes, cooled to 0° C. and 26.6 mg of sodium borohydride (0.7 mmole, 4 eq.) was added. After stirring at 0° C. for 15 minutes, the reaction mixture was poured into 100 ml of a saturated ammonium chloride solution and extracted with three 30 ml portions of ether. The combined ethereal extract was dried over anhydrous MgSO₄ and concentrated.

Separation and purification was done on a LPS-1 silica gel column, eluting with 40% ether in hexanes to give 91.5 mg of title J allylic alcohol.

EXAMPLE 2
[1α,2β,3β(1E,3R),4α]-5-[[3-(3-Hydroxy-4,4-dimethyl-1-octenyl)-7-oxabicyclo[2.2.1]hept-2-yl]methoxy]pentanoic acid To a solution of 91.5 mg of the Example 1 alcohol (0.23 mmole) in 16 ml of THF and 4 ml of H₂O at 0° C. was added dropwise 2.3 ml of 1N lithium hydroxide solution. The mixture was stirred at 25° C. for 3 hours. THF was evaporated. The residue was diluted with 5 ml of H₂O and acidified to pH 3 with a saturated oxalic acid solution. This was extracted with three 20 ml portions of ether. The ethereal extract was washed with 10 ml of H₂O, dried over anhydrous MgSO₄ and concentrated to give 93 mg of a crude oil.

Flash chromatography on a Merck silica gel 60 column and eluting with 3% MeOH/CH₂Cl₂ gave 61 mg of title product as a clear oil after 2 days under high vacuum.

TLC: Silica gel; 5% MeOH/CH₂Cl₂; $R_f \sim 0.40$

Anal. Calcd for $C_{22}H_{38}O_5$: C, 69.07; H, 10.01; Found: C, 68.54; H, 9.97.

EXAMPLE 3
[1α,2β,3β(1E,3R),4α]-4-[[3-(3-Hydroxy-4,4-dimethyl-1-octenyl)-7-oxabicyclo[2.2.1]hept-2-yl]ethoxy]-butanoic acid, methyl ester

A.
(1α,2β,3β,4α)-Cis-exo-2-hydroxymethyl-3-chlorooxycarbonyloxymethyl-7-oxabicyclo[2.2.1]heptane and

B.
(1α,2β,3β,4α)-Cis-exo-7-oxabicyclo[2.2.1]heptane-2,3-dimethanol carbonate To a solution of 10 g of the diol from Example 1, Part A (63.2 mmole) in 40 ml dry THF at 0° C. was added with stirring 55 ml of a 12.5% by weight solution of phosgene in toluene (63.2 mmole, 1 eq.) dropwise over a period of 30 minutes. Argon was then bubbled through the reaction mixture for 15 minutes. The mixture was concentrated to give title A compound in the form of a crude oil.

The title A oil was dissolved in 30 ml of dry CH₂Cl₂ and cooled to −50° C. To this solution was added dropwise a solution of 10 ml pyridine in 10 ml CH₂Cl₂. The mixture was stirred for 10 minutes and quenched with H₂O. The mixture was then extracted thoroughly with CH$_2$Cl$_2$. The organic extract was dried over MgSO$_4$ and concentrated to give the title B cyclic carbonate as a crystalline solid (10.7g).

C.
(1α,2β,3β,4α)-Cis-exo-2-hydroxymethyl-3-isopropyloxycarbonyloxymethyl-7-oxabicyclo[2.2.1]heptane A mixture of 10.7 g title B cyclic carbonate (58.1 mmole) in 100 ml isopropanol was refluxed for 24 hours. Excess isopropanol was removed under reduced pressure to give 14.4 g title C hydroxycarbonate as a viscous oil.

D.
(1α,2β,3β,4α)-Cis-exo-2-p-toluenesulfonyloxymethyl-3-isopropyloxycarbonyloxymethyl-7-oxabicyclo[2.2.1]heptane To a solution of 19.7 g title C hydroxy carbonate (80 mmole) in 30 ml CH$_2$Cl$_2$ and 12.8 ml pyridine (160 mmole, 2 eq.) was added 18.5 g p-toluenesulfonyl chloride (96 mmole, 1.2 eq.). The mixture was stirred at 25° C. for 36 hours, then diluted with 200 ml ether, and washed with 100 ml. The organic layer was dried over MgSO$_4$ and concentrated to give 32.8 g of crude title D tosylate.

(1α,2β,3β,4α)-Cis-exo-2-Cyanomethyl-3-isopropyloxycarbonyloxymethyl-7-oxabicyclo[2.2.1]heptane To a solution of 24.0 g title D crude tosylate (60 mmole) in 20 ml DMSO was added with stirring 6.0 g powdered sodium cyanide (120 mmole, 2 eq.). The mixture was heated at 90°–95° C. for 1.5 hours under an argon atmosphere. The cooled mixture was diluted with 50 ml water and extracted with five 100 ml portions of ether. The ethereal extracts were dried over anhydrous MgSO$_4$ and filtered through a bed of florosil. The filtrate was concentrated, and the residue was recrystallized with ether/hexanes to give 8.4 g title E cyanocarbonate as a light yellow crystalline solid.

F.
(1α,2β,3β,4α)-3-Cyanomethyl-2-hydroxymethyl-7-oxabicyclo[2.2.1]heptane To 8.4 g title E cyanocarbonate (33.2 mmole) was added 75 ml of a 1% solution of potassium carbonate in methanol-water (2:1). The reaction mixture was stirred at 25° C. for 6 hours then acidified with 2N HCl solution, saturated with sodium chloride and extracted with six 100 ml portions of CH$_2$Cl$_2$. The combined organic layer was dried over anhydrous MgSO$_4$ and concentrated to give 5.5 g of crude title F cyanoalcohol as a light yellow oil.

G.
(1α,2β,3β,4α)-3-Cyanomethyl-2-benzyloxymethyl-7-oxabicyclo[2.2.1]heptane To a slurry of 1.1 g of sodium hydride (21 mmole, 50% oil dispersion in 25 ml of dry DMF at 0° C. was added a solution of 3.34 g of title F cyanoalcohol (20 mmole) in 10 ml of DMF over a period of 10 minutes. After stirring for an additional 15 minutes, 3.6 g of benzyl bromide was added dropwise. The reaction mixture was stirred for 30 minutes at 0° C. and 3 hours at 25° C. then quenched with a saturated ammonium chloride solution, and diluted with ether. The organic layer was washed with brine. The combined aqueous layer was re-extracted with ether. The combined organic layer was dried over anhydrous MgSO$_4$ and concentrated to leave an oil. The crude oil was chromatographed on a silica gel column, eluting with 10–20% ethyl acetate in hexanes to give 4.43 g of the title G benzyl ether.

H.
(1α,2β,3β,4α)-[3-Benzyloxymethyl-7-oxabicyclo[2.2.1]hept-2-yl]acetaldehyde and

I.
(1α,2β,3β,4α)-[3-Benzyloxymethyl-7-oxabicyclo[2.2.1]hept-2-yl]ethanol To a solution of 4.43 g of title G nitrile (17.24 mmole) in 20 ml of dry toluene at −78° C. was added dropwise 20 ml of a 25% by weight solution of diisobutylaluminum hydride in toluene (35 mmole, 2 eq.). After stirring at −78° C. for 4 hours the reaction was quenched with a saturated ammonium chloride solution. The mixture was warmed to 25° C. and 50 ml of a 1N aqueous hydrochloric acid solution was added. The organic layer was separated and the aqueous layer was extracted several times with ether. The combined organic extract was dried over anhydrous MgSO$_4$ and concentrated to give 4.55 g of crude title H aldehyde.

To the above crude title H aldehyde (ca. 17.24 mmole) in 30 ml of dry THF at 0° C. was added 380 mg of 95% pure lithiumaluminum hydride (10 mmole, 2.3 eq.) portionwise. After stirring while warming to 25° C. over a period of 1 hour, the reaction was quenched with a saturated sodium sulfate solution. Solid anhydrous MgSO$_4$ was added and the mixture was filtered. The filtrate was concentrated to give 4.25 g of title I alcohol as a colorless oil.

J.
(1α,2β,3β,4α)-4-[[3-Benzyloxymethyl-7-oxabicyclo[2.2.1]hept-2-yl]ethoxy]butanol, t-butyldimethylsilyl ether To a mixture of 4.5 g of powdered potassium hydroxide (82.6 mmole, 10 eq.) in 20 ml of dry xylene was added a solution of 2.0 g of title I alcohol (8.26 mmole) in 10 ml of xylene. The mixture was heated to reflux and 15 ml of xylene was distilled off.

To the cooled remaining solution was added a solution of 4.0 g of 4-tert-butyldimethylsilyloxy n-butylmesylate in 10 ml of xylene. The resulting mixture was refluxed for 1 hour, cooled to 25° C. and diluted with 300 ml of ether. The ethereal solution was washed with two 50 ml portions of water, dried over anhydrous MgSO$_4$ and concentrated. The residue was purified on a silica gel column, eluting with 20% ether in hexanes to give 1.4 g of title J compound as a yellow oil.

K.
(1α,2β,3β,4α)-[[3-Benzyloxymethyl-7-oxabicyclo[2.2.1]hept-2-yl]ethoxy]butanol To 1.2 g of title J compound (2.68 mmole) in 5 ml of THF at 0° C. was added 1.1 g of tetra-n-butylammonium fluoride (3.46 mmole, 1.3 eq.). The mixture was stirred at 0° C. for 1 hour and at 25° C. for 1 hour then diluted with 50 ml of ether. The ethereal solution was washed with two 10 ml portions of H$_2$O, 10 ml of brine, dried over anhydrous MgSO$_4$ and concentrated to give crude title K alcohol as an oil. This was used without purification.

L.
(1α,2β,3β,4α)-4-[[3-Benzyloxymethyl-7-oxabicyclo[2.2.1]hept-2-yl]ethoxy]butanoic acid and

M.
(1α,2β,3β,4α)-4-[[3-Benzyloxymethyl-7-oxabicyclo[2.2.1]hept-2-yl]ethoxy]butanoic acid, methyl ester To crude title K alcohol in 30 ml of acetone at 0° C. was added dropwise a solution of 2.6M Jones' reagent until the reaction mixture remained orange. The mixture was stirred for an additional 30 minutes at 0° C. then quenched with isopropanol and diluted with 200 ml of ether. Anhydrous sodium acetate along with anhydrous magnesium sulfate was added. The mixture was stirred for 15 minutes at 25° C. and filtered through a bed of florosil. The filtrates were concentrated. The residue was treated with 200 ml of saturated NaHCO$_3$ solution and extracted with two 50 ml portions of ether. The aqueous layer was acidified with concentrated HCl, saturated with solid NaCl and extracted with five 100 ml portions of CH$_2$Cl$_2$, dried over anhydrous MgSO$_4$ and concentrated to give title L acid as an oil.

The above title I acid, dissolved in 30 ml of ether, was treated with an ethereal solution of diazomethane to give an oil which was purified on a silica gel column, eluting with 20% EtOAc in hexanes to yield 500 mg of pure title M ester.

N.
(1α,2β,3β,4α)-4-[[3-Hydroxymethyl-7-oxabicyclo[2.2.1]hept-2-yl]ethoxy]butanoic acid, methyl ester, and

O.
(1α,2β,3β,4α)-4-[[3-Formyl-7-oxabicyclo[2.2.1]hept-2-yl]ethoxy]butanoic acid, methyl ester A mixture of 500 mg of title M ester (1.38 mmole), 250 mg of 10% palladium over carbon in 10 ml of ethyl acetate and 1 ml of glacial acetic acid was shaken in a Parr bottle under 40 lbs. of hydrogen pressure at 25° C. for 18 hours. The mixture was filtered through a bed of Celite and concentrated to give 242 mg of title N alcohol as an oil.

To 1.9 ml of pyridine (13.3 mmole, 15 eq.) in 20 ml of dry CH$_2$Cl$_2$ at 25° C. was added 1.3 g of chromium trioxide (13.3 mmole, 15 eq.). The mixture was stirred for 1 hour at 25° C. 2 g of Celite along with a solution of 242 mg of title N alcohol (0.89 mmole) in 5 ml of CH$_2$Cl$_2$ was added. After stirring for 30 minutes at 25° C., the reaction mixture was diluted with 100 ml of ether and filtered through a bed of florosil. The filtrate was concentrated to yield 200 mg of title O aldehyde as an oil.

P.
(1α,2β,3β(4E),4α)-4-[[3-(3-Oxo-4,4-dimethyl-1-octenyl)-7-oxabicyclo[2.2.1]hept-2-yl]ethoxy]butanoic acid, methyl ester To a slurry of 76 mg of sodium hydride (1.6 mmole, 2.2 eq., 50% dispersion in mineral oil) in 10 ml of DME was added at 0° C. 561 mg of 2-oxo-3,3-dimethylheptyl dimethyl phosphonate (2.18 mmole, 3.0 eq.). The mixture was stirred for 1 hour at 25° C., cooled to 0° C. and a solution of 200 mg of title O aldehyde in 5 ml of DME added. The reaction mixture was stirred at 25° C. for 3 hours then quenched with glacial acetic acid and concentrated. The residue was diluted with 50 ml of ether and washed with two 15 ml portions of saturated NaHCO$_3$, 15 ml of H$_2$O, dried over anhydrous MgSO$_4$ and concentrated to give 650 mg of title P compound as a crude oil. This oil was used in the next reaction without further purification.

Q.
[1α,2β,3β(1E,3R),4α]-4-[[3-(3-Hydroxy-4,4-dimethyl-1-octenyl)-7-oxabicyclo[2.2.1]hept-2-yl]ethoxy]-butanoic acid, methyl ester To 650 mg of crude title P enone (ca. 0.073 mmole) in 3 ml of dry methanol at 25° C. was added 268 mg of cerium trichloride (0.73 mm, 1 eq.). The mixture was stirred at 25° C. for 10 minutes, cooled to 0° C. and 27.7 mg of sodium borohydride (0.73 mmole, 4 eq.) was added. After stirring at 0° C. for 15 minutes, the reaction mixture was poured into 100 ml of a saturated ammonium chloride solution and extracted with three 30 ml portions of ether. The combined ethereal solution was dried over anhydrous MgSO$_4$ and concentrated.

Separation and purification was done on a LPS-1 silica gel column, eluting with 40% ether in hexanes to give 128 mg of title Q allylic alcohol.

EXAMPLE 4
[1α,2β,3β(1E,3R),4α]-4-[[3-(3-Hydroxy-4,4-dimethyl-1-octenyl)-7-oxabicyclo[2.2.1]hept-2-yl]ethoxy]-butanoic acid To a solution of 128 mg of Example 3, title Q allylic alcohol (0.32 mmole) in 4 ml of THF and 1 ml of H$_2$O at 0° C. was added dropwise 3.2 ml of 1N lithium hydroxide solution. The mixture was stirred at 25° C. for 3 hours. THF was evaporated. The residue was diluted with 5 ml of H$_2$O and acidified to pH 3 with a saturated oxalic acid solution. This was extracted with three 20 ml portions of ether. The ethereal extracts were washed with 10 ml of H$_2$O, dried over anhydrous MgSO$_4$ and concentrated to give 120 mg of title product as a clear oil.

TLC: silica gel; 5% MeOH/CH$_2$Cl$_2$; R$_f$~0.35.

Anal Calcd for C$_{22}$H$_{38}$O$_5$, 0.3 H$_2$O: C, 68.10; H, 10.03; Found: C, 68.10; H, 9.89

EXAMPLE 5
[1α,2β,3β(1E,3R),4α]-6-[[3-(3-Hydroxy-4,4-dimethyl-1-octenyl)-7-oxabicyclo[2.2.1]hept-2-yl]methoxy]hexanoic acid Following the procedure of Examples 1 and 2 except substituting 6-t-butyldimethylsilyloxy n-hexyl mesylate for 5-t-butyldimethylsilyloxy n-pentyl mesylate, the title compound is obtained.

EXAMPLE 6
[1α,2β,3β(1E,3R),4α]-3-[[3-(3-Hydroxy-4,4-dimethyl-1-octenyl)-7-oxabicyclo[2.2.1]hept-2-yl]methoxy]propionic acid Following the procedure of Examples 1 and 2 except substituting 3-t-butyldimethylsilyloxy propyl mesylate for 5-t-butyldimethylsilyloxy n-pentyl mesylate, the title compound is obtained.

EXAMPLE 7
[1α,2β,3β(1E,3R),4α]-2-[[3-(3-Hydroxy-4,4-dimethyl-1-octenyl)-7-oxabicyclo[2.2.1]hept-2-yl]methoxy]acetic acid Following the procedure of Examples 1 and 2 except substituting 2-t-butyldimethylsilyloxy ethyl mesylate for 5-t-butyldimethylsilyloxy n-pentyl mesylate, the title compound is obtained.

EXAMPLE 8

[1α,2β,3β(1E,3R),4α]-4-[[3-(3-Hydroxy-4,4-dimethyl-1-octenyl)-7-oxabicyclo[2.2.1]hept-2-yl]methoxy]butanoic acid Following the procedure of Examples 1 and 2 except substituting 4-t-butyldimethylsilyloxy n-butyl mesylate for 5-t-butyldimethylsilyloxy n-pentyl mesylate, the title compound is obtained.

EXAMPLE 9

[1α,2β,3β(1E,3R),4α]-8-[[3-(3-Hydroxy-4,4-dimethyl-1-octenyl)-7-oxabicyclo[2.2.1]hept-2-yl]methoxy]octanoic acid Following the procedure of Examples 1 and 2 except substituting 8-t-butyldimethylsilyloxy n-octyl mesylate for 5-t-butyldimethylsilyloxy n-pentyl mesylate, the title compound is obtained.

EXAMPLE 10

[1α,2β,3β(1E,3R),4α]-5-[[3-(3-Hydroxy-1-octenyl)-7-oxabicyclo[2.2.1]hept-2-yl]methoxy]pentanoic acid Following the procedure of Examples 1 and 2 except substituting 2-oxo-heptyl dimethylphosphonate for 2-oxo-3,3-dimethylheptyldimethylphosphonate, the title compound is obtained.

EXAMPLE 11

[1α,2β,3β(1E,3R),4α]-5-[[3-(3-Hydroxy-1-heptenyl)-7-oxabicyclo[2.2.1]hept-2-yl]methoxy]pentanoic acid Following the procedure of Examples 1 and 2 except substituting 2-oxo-hexyl dimethylphosphonate for 2-oxo-3,3-dimethylheptyldimethylphosphonate, the title compound is obtained.

EXAMPLE 12

[1α,2β,3β(1E,3R),4α]-5-[[3-(3-Hydroxy-3-cyclohexyl-1-propenyl)-7-oxabicyclo[2.2.1]hept-2-yl]methoxy]pentanoic acid Following the procedure of Examples 1 and 2 except substituting 2-oxo-cyclohexyl dimethylphosphonate for 2-oxo-3,3-dimethylheptyldimethylphosphonate, the title compound is obtained.

EXAMPLE 13

[1α,2β,3β(1E,3R),4α]-5-[[3-(3-Hydroxy-3-phenyl-1-propenyl)-7-oxabicyclo[2.2.1]hept-2-yl]methoxy]pentanoic acid Following the procedure of Examples 1 and 2 except substituting 2-oxo-phenyl dimethylphosphonate for 2-oxo-3,3-dimethylheptyldimethylphosphonate, the title compound is obtained.

EXAMPLE 14

[1α,2β,3β(1E,3R),4α]-5-[[3-(3-Hydroxy-3-benzyl-1-propenyl)-7-oxabicyclo[2.2.1]hept-2-yl]methoxy]pentanoic acid Following the procedure of Examples 1 and 2 except substituting 2-oxo-benzyl dimethylphosphonate for 2-oxo-3,3-dimethylheptyldimethylphosphonate, the title compound is obtained.

EXAMPLE 15

[1α,2β,3β(1E,3R),4α]-6-[[3-(3-Hydroxy-1-octenyl)-7-oxabicyclo[2.2.1]hept-2-yl]methoxy]hexanoic acid Following the procedure of Examples 1 and 2 except substituting 6-t-butyldimethylsilyloxy n-hexyl mesylate for 5-t-butyldimethylsilyloxy n-pentylmesylate and substituting 2-oxo-heptyl dimethylphosphonate for 2-oxo-3,3-dimethylheptyldimethylphosphonate, the title compound is obtained.

EXAMPLE 16

[1α,2β,3β(1E,3R),4α]-3-[[3-(3-Hydroxy-1-heptenyl)-7-oxabicyclo[2.2.1]hept-2-yl]methoxy]propionic acid Following the procedure of Examples 1 and 2 except substituting 3-t-butyldimethylsilyloxy propyl mesylate for 5-t-butyldimethylsilyloxy n-pentylmesylate and substituting 2-oxo-hexyl dimethylphosphonate for 2-oxo-3,3-dimethylheptyldimethylphosphonate, the title compound is obtained.

EXAMPLE 17

[1α,2β,3β(1E,3R),4α]-2-[[3-(3-Hydroxy-3-cyclohexylmethyl-1-propenyl)-7-oxabicyclo[2.2.1]hept-2-yl]methoxy]acetic acid Following the procedure of Examples 1 and 2 except substituting 2-t-butyldimethylsilyloxy ethyl mesylate for 5-t-butyldimethylsilyloxy n-pentylmesylate and substituting 2-oxo-cyclohexylmethyl dimethylphosphonate for 2-oxo-3,3-dimethylheptyldimethylphosphonate, the title compound is obtained.

EXAMPLE 18

[1α,2β,3β(1E,3R),4α]-4-[[3-(3-Hydroxy-3-benzyl-1-propenyl)-7-oxabicyclo[2.2.1]hept-2-yl]methoxy]butanoic acid Following the procedure of Examples 1 and 2 except substituting 4-t-butyldimethylsilyloxy n-butyl mesylate for 5-t-butyldimethylsilyloxy n-pentylmesylate and substituting 2-oxo-benzyl dimethylphosphonate for 2-oxo-3,3-dimethylheptyldimethylphosphonate, the title compound is obtained.

EXAMPLE 19

[1α,2β,3β(1E,3R),4α]-8-[[3-(3-Hydroxy-3-cyclopentyl-1-propenyl)-7-oxabicyclo[2.2.1]hept-2-yl]methoxy]octanoic acid Following the procedure of Examples 1 and 2 except substituting 8-t-butyldimethylsilyloxy n-octyl mesylate for 5-t-butyldimethylsilyloxy n-pentylmesylate and substituting 2-oxo-cyclopentyl dimethylphosphonate for 2-oxo-3,3-dimethylheptyldimethylphosphonate, the title compound is obtained.

EXAMPLE 20

[1α,2β,3β(1E,3R),4α]-6-[[3-(3-Hydroxy-4,4-dimethyl-1-octenyl)-7-oxabicyclo[2.2.1]hept-2-yl]ethoxy]hexanoic acid Following the procedure of Examples 3 and 4 except substituting 6-t-butyldimethylsilyloxy n-hexyl mesylate for 5-t-butyldimethylsilyloxy n-pentyl mesylate, the title compound is obtained.

EXAMPLE 21

[1α,2β,3β(1E,3R),4α]-3-[[3-(3-Hydroxy-4,4-dimethyl-1-octenyl)-7-oxabicyclo[2.2.1]hept-2-yl]ethoxy]propionic acid Following the procedure of Examples 3 and 4 except substituting 3-t-butyldimehylsilyloxy propyl mesylate for 5-t-butyldimethylsilyloxy n-pentyl mesylate, the title compound is obtained.

EXAMPLE 22

[1α,2β,3β(1E,3R),4α]-2-[[3-(3-Hydroxy-4,4-dimethyl-1-octenyl)-7-oxabicyclo[2.2.1]hept-2-yl]ethoxy]acetic acid Following the procedure of Examples 3 and 4 except substituting 2-t-butyldimethylsilyloxy ethyl mesylate for 5-t-butyldimethylsilyloxy n-pentyl mesylate, the title compound is obtained.

EXAMPLE 23

[1α,2β,3β(1E,3R),4α]-4-[[3-(3-Hydroxy-4,4-dimethyl-1-octenyl)-7-oxabicyclo[2.2.1]hept-2-yl]ethoxy]-butanoic acid Following the procedure of Examples 3 and 4 except substituting 4-t-butyldimethylsilyloxy n-butyl mesylate for 5-t-butyldimethylsilyloxy n-pentyl mesylate, the title compound is obtained.

EXAMPLE 24

[1α,2β,3β(1E,3R),4α]-8-[[3-(3-Hydroxy-4,4-dimethyl-1-octenyl)-7-oxabicyclo[2.2.1]hept-2-yl]ethoxy]octanoic acid Following the procedure of Examples 3 and 4 except substituting 8-t-butyldimethylsilyloxy n-octyl mesylate for 5-t-butyldimethylsilyloxy n-pentyl mesylate, the title compound is obtained.

EXAMPLE 25

[1α,2β,3β(1E,3R),4α]-4-[[3-(3-Hydroxy-1-octenyl)-7-oxabicyclo[2.2.1]hept-2-yl]ethoxy]butanoic acid Following the procedure of Examples 3 and 4 except substituting 2-oxo-heptyl dimethylphosphonate for 2-oxo-3,3-dimethylheptyldimethylphosphonate, the title compound is obtained.

EXAMPLE 26

[1α,2β,3β(1E,3R),4α]-4-[[3-(3-Hydroxy-1-heptenyl)-7-oxabicyclo[2.2.1]hept-2-yl]ethoxy]butanoic acid Following the procedure of Examples 3 and 4 except substituting 2-oxo-hexyl dimethylphosphonate for 2-oxo-3,3-dimethylheptyldimethylphosphonate, the title compound is obtained.

EXAMPLE 27

[1α,2β,3β(1E,3R),4α]-4-[[3-(3-Hydroxy-3-cyclohexyl-1-propenyl)-7-oxabicyclo[2.2.1]hept-2-yl]ethoxy]-butanoic acid Following the procedure of Examples 3 and 4 except substituting 2-oxo-cyclohexyl dimethylphosphonate for 2-oxo-3,3-dimethylheptyldimethylphosphonate, the title compound is obtained.

EXAMPLE 28

[1α,2β,3β(1E,3R),4α]-4-[[3-(3-Hydroxy-3-phenyl-1-propenyl)-7-oxabicyclo[2.2.1]hept-2-yl]ethoxy]butanoic acid Following the procedure of Examples 3 and 4 except substituting 2-oxo-phenyl dimethylphosphonate for 2-oxo-3,3-dimethylheptyldimethylphosphonate, the title compound is obtained.

EXAMPLE 29

[1α,2β,3β(1E,3R),4α]-4-[[3-(3-Hydroxy-3-benzyl-1-propenyl)-7-oxabicyclo[2.2.1]hept-2-yl]ethoxy]butanoic acid Following the procedure of Examples 3 and 4 except substituting 2-oxo-benzyl dimethylphosphonate for 2-oxo-3,3-dimethylheptyldimethylphosphonate, the title compound is obtained.

EXAMPLE 30

[1α,2β,3β(1E,3R),4α]-6-[[3-(3-Hydroxy-1-octenyl)-7-oxabicyclo[2.2.1]hept-2-yl]ethoxy]hexanoic acid Following the procedure of Examples 3 and 4 except substituting 6-t-butyldimethylsilyloxy n-hexyl mesylate for 5-t-butyldimethylsilyloxy n-pentylmesylate and substituting 2-oxo-heptyl dimethylphosphonate for 2-oxo-3,3-dimethylheptyldimethylphosphonate, the title compound is obtained.

EXAMPLE 31

[1α,2β,3β(1E,3R),4α]-3-[[3-(3-Hydroxy-1-heptenyl)-7-oxabicyclo[2.2.1]hept-2-yl]ethoxy]propionic acid Following the procedure of Examples 3 and 4 except substituting 3-t-butyldimethylsilyloxy propyl mesylate for 5-t-butyldimethylsilyloxy n-pentylmesylate and substituting 2-oxo-hexyl dimethylphosphonate for 2-oxo-3,3-dimethylheptyldimethylphosphonate, the title compound is obtained.

EXAMPLE 32

[1α,2β,3β(1E,3R),4α]-2-[[3-(3-Hydroxy-3-cyclohexylmethyl-1-propenyl)-7-oxabicyclo[2.2.1]hept-2-yl]ethoxy]acetic acid Following the procedure of Examples 3 and 4 except substituting 2-t-butyldimethylsilyloxy ethyl mesylate for 5-t-butyldimethylsilyloxy n-pentylmesylate and substituting 2-oxo-cyclohexylmethyl dimethylphosphonate for 2-oxo-3,3-dimethylheptyldimethylphosphonate, the title compound is obtained.

EXAMPLE 33

[1α,2β,3β(1E,3R),4α]-4-[[3-(3-Hydroxy-3-benzyl-1-propenyl)-7-oxabicyclo[2.2.1]hept-2-yl]ethoxy]butanoic acid Following the procedure of Examples 3 and 4 except substituting 4-t-butyldimethylsilyloxy n-butyl mesylate for 5-t-butyldimethylsilyloxy n-pentylmesylate and substituting 2-oxo-benzyl dimethylphosphonate for 2-oxo-3,3-dimethylheptyldimethylphosphonate, the title compound is obtained.

EXAMPLE 34

[1α,2β,3β(1E,3R),4α]-8-[[3-(3-Hydroxy-3-cyclopentyl-1-propenyl)-7-oxabicyclo[2.2.1]hept-2-yl]ethoxy]octanoic acid Following the procedure of Examples 3 and 4 except substituting 8-t-butyldimethylsilyloxy n-octyl mesylate for 5-t-butyldimethylsilyloxy n-pentylmesylate and substituting 2-oxo-cyclopentyl dimethylphosphonate for 2-oxo-3,3-dimethylheptyldimethylphosphonate, the title compound is obtained.

EXAMPLE 35

[1α,2β,3β(1E,3R),4α]-3-[[3-(3-Hydroxy-4,4-dimethyl-1-octenyl)-7-oxabicyclo[2.2.1]hept-2-yl]propoxy]propionic acid

A.
(1α,2β,3β,4α)-3-Benzyloxymethyl-2-p-toluenesulfonyloxyethyl-7-oxabicyclo[2.2.1]heptane Following the procedure of Example 3, part D, except substituting Example 3, title I alcohol for Example 3, title C alcohol, the title A compound is obtained.

B.
(1α,2β,3β,4α)-3-Benzyloxymethyl-2-cyanoethyl-7-oxabicyclo-[2.2.1]heptane Following the procedure of Example 3, part E, except substituting Example 35, title A tosylate for Example 3, title D tosylate, the title B compound is obtained.

C.
(1α,2β,3β,4α)-[3-Benzyloxymethyl-7-oxabicyclo[2.2.1]hept-2-yl]propionaldehyde Following the procedure of Example 3, part H, except substituting Example 35, title B cyanide for Example 3, title G cyanide, the title C compound is obtained.

D.
(1α,2β,3β,4α)-[3-Benzyloxymethyl-7-oxabicyclo[2.2.1]hept-2-yl]propanol

Following the procedure of Example 3, part I, except substituting Example 35, title C aldehyde for Example 3, title H aldehyde, the title D compound is obtained.

E.
(1α,2β,3β,4α)-3-[[3-Benzyloxymethyl-7-oxabicyclo[2.2.1]hept-2-yl]propioxy]propanol, t-butyldimethylsilyl ether Following the procedure of Example 3, part J, except substituting Example 35, title D alcohol for Example 3, title I alcohol, and substituting 3-t-butyldimethylsilyloxy n-propylmesylate for 4-t-butylsilyloxy n-butylmesylate, the title E compound is obtained.

F.
[1α,2β,3β(1E,3R),4α]-3-[[3-Hydroxy-4,4-dimethyl-1-octenyl-7-oxabicyclo[2.2.1]hept-2-yl]propoxy]propionic acid Following the procedure of Example 3, parts K–Q and Example 4, except substituting Example 35, title E compound for Example 3, title J compound, the title F acid is obtained.

EXAMPLE 36

[1α,2β,3β(1E,3R),4α]-2-[[3-(3-Hydroxy-4,4-dimethyl-1-octenyl)-7-oxabicyclo[2.2.1]hept-2-yl]butoxy]acetic acid

A.
(1α,2β,3β,4α)-[3-Benzyloxymethyl-7-oxabicyclo[2.2.1]hept-2-yl]butanol

Following the procedure of Example 35, parts A–D, except substituting Example 35, title D alcohol for Example 3, title I alcohol, the title A alcohol is obtained.

B.
(1α,2β,3β,4α)-2-[[3-Benzyloxymethyl-7-oxabicyclo[2.2.1]hept-2-yl]butoxy]ethanol, t-butyldimethylsilyl ether Following the procedure of Example 3, part J, except substituting Example 36, title A alcohol for Example 3, title I alcohol and substituting 2-t-butyldimethylsilyloxy ethylmesylate for 4-t-butyldimethylsilyloxy n-butylmesylate, the title B alcohol is obtained.

C.
[1α,2β,3β(1E,3R),4α]-2-[[3-(3-Hydroxy-4,4-dimethyl-1-octenyl)-7-oxabicyclo[2.2.1]hept-2-yl]butoxy]acetic acid Following the procedure of Example 3, parts K–Q and Example 4, except substituting Example 36, title B compound for Example 3, title J compound, the title acid is obtained.

EXAMPLE 37

[1α,2β,3β(1E,3R),4α]-5-[[3-(3-Hydroxy-4,4-dimethyl-1-octenyl)-7-oxabicyclo[2.2.1]hept-2-yl]methoxy]-2-pentanoic acid Following the procedure of Examples 1 and 2, except substituting 5-t-butyldimethylsilyloxy-3-pentenylmesylate for 5-t-butyldimethylsilyloxy n-pentylmesylate, the title acid is obtained.

EXAMPLE 38

[1α,2β,3β(3R),4α]-5-[[3-(3-Hydroxy-4,4-dimethyloctyl)-7-oxabicyclo[2.2.1]hept-2-yl]methoxy]pentanoic acid

A.
[1α,2β,3β(3R),4α]-5-[[3-(3-Hydroxy-4,4-dimethyloctyl)-7-oxabicyclo[2.2.1]hept-2-yl]methoxy]pentanoic acid, methyl ester To a solution of 396 mg of Example 1, title J allylic alcohol (1 mmole) in 10 ml of absolute ethanol is added with stirring 40 mg of 10% palladium on charcoal. The reaction mixture is hydrogenated under an atmosphere of hydrogen, where upon it is filtered and the filtrate is concentrated under reduced pressure to give title A alcohol ester.

B.
[1α,2β,3β(3R),4α]-5-[[3-(3-Hydroxy-4,4-dimethyloctyl)-7-oxabicyclo[2.2.1]hept-2-yl]methoxy]pentanoic acid Following the procedure of Example 2, except substituting Example 38, title A alcohol ester for Example 1, title J alcohol ester, the title acid is obtained.

EXAMPLE 39

[1α,2β,3β(3R),4α]-4-[[3-(3-Hydroxy-4,4-dimethyloctyl)-7-oxabicyclo[2.2.1]hept-2-yl]ethoxy]butanoic acid

A.

[1α,2β,3β(3R),4α]-4-[[3-(3-Hydroxy-4,4-dimethyloctyl)-7-oxabicyclo[2.2.1]hept-2-yl]ethoxy]butanoic acid, methyl ester To a solution of 396 mg of Example 3, title Q, allylic alcohol (1 mmole) in 10 ml of abosolute ethanol is added 40 mg of 10% palladium on charcoal. The reaction mixture is hydrogenated under a hydrogen atmosphere, where upon the catalyst is filtered off and the filtrate is concentrated under reduced pressure to give title A alcohol ester.

B.

[1α,2β,3β(3R),4α]-4-[[3-(3-Hydroxy-4,4-dimethyloctyl)-7-oxabicyclo[2.2.1]hept-2-yl]methoxy]butanoic acid Following the procedure of Example 4, except substituting Example 39, title A alcohol ester for Example 3, title Q alcohol ester, the title acid is obtained.

EXAMPLE 40

[1α,2β,3β(1E,3R),4α]-4-[[3-(3-Hydroxy-4,4-dimethyloctenyl)-7-oxabicyclo[2.2.1]hept-2-yl]ethoxy]-2-butenoic acid Following the procedure of Examples 3 and 4, except substituting 4-t-butyldimethylsilyloxy-2-butenylmesylate for 4-t-butyldimethylsilyloxy-n-butylmesylate, the title acid is obtained.

What is claimed is:

1. A compound of the structure

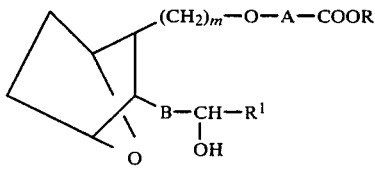

including all stereoisomers thereof, wherein m is 1 to 4, A is $(CH_2)_n$ or $—(CH_2)_{n'}—CH=CH—$; n is 1 to 8; n' is 1 or 2; B is $—CH=CH—$ or $—(CH_2)_2—$; R is H, lower alkyl or alkali metal; and $R^1$ is lower alkyl, aryl, arylalkyl, cycloalkyl or cycloalkylalkyl; wherein the term alkyl by itself or as part of another group contains up to 12 carbon atoms and may be unsubstituted or substituted with halo, trifluoromethyl or alkoxy; the term aryl by itself or as part of another group contains 6 to 10 carbons in the ring portion and may be unsubstituted or substituted with lower alkyl, halogen or lower alkoxy; and the term cycloalkyl by itself or as part of another group contains 3 to 12 carbons and may be unsubstituted or substituted with 1 or 2 halogens, 1 or 2 lower alkyl groups and/or 1 or 2 lower alkoxy groups.

2. The compound as defined in claim 1 wherein B is $—CH=CH—$.

3. The compound as defined in claim 1 wherein R is H.

4. The compound as defined in claim 1 wherein A is $(CH_2)_n$ and n is 2 to 5.

5. The compound as defined in claim 1 wherein n is 3 or 4.

6. The compound as defined in claim 1 wherein B is $—CH=CH—$, m is 1 or 2, A is $(CH_2)_n$, n is 3 or 4, R is H and $R^1$ is lower alkyl.

7. The compound as defined in claim 1 wherein $R^1$ is butyl, pentyl, hexyl or heptyl including all isomers thereof.

8. The compound as defined in claim 1 having the name [1α,2β,3β(1E,3R),4α]-5-[[3-(3-hydroxy-4,4-dimethyl-1-octenyl)-7-oxabicyclo[2.2.1]hept-2-yl]methoxy]pentanoic acid or the methyl ester thereof, including all stereoisomers thereof.

9. The compound as defined in claim 1 having the name [1α,2β,3β(1E,3R),4α]-4-[[3-(3-hydroxy-4,4-dimethyl-1-octenyl)-7-oxabicyclo[2.2.1]hept-2-yl]ethoxy]butanoic acid or the methyl ester thereof, including all stereoisomers thereof.

10. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

11. The method as defined in claim 10 wherein said compound is administered in an amount within the range of from about 1 to about 100 mg/kg.

12. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

13. A method of inhibiting platelet aggregation which comprises administering to a mammalian host an effective amount of a compound as defined in claim 1 or a pharmaceutically acceptable salt thereof.

14. A method of inhibiting bronchoconstriction associated with asthma, while comprises administering to a mammalian host an effective amount of a compound as defined in claim 1 or a pharmaceutically acceptable salt thereof.

15. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,513,103
DATED : April 23, 1985
INVENTOR(S) : Jagabandhu Das, et al.

It is certified that error appears in the above—identified patent and that said Letters Patent is hereby corrected as shown below:

Column 12, structure IH should read

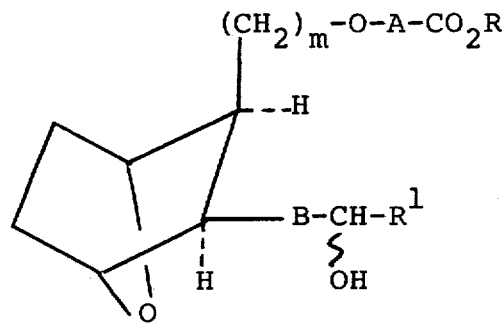

Column 12, structure II should read

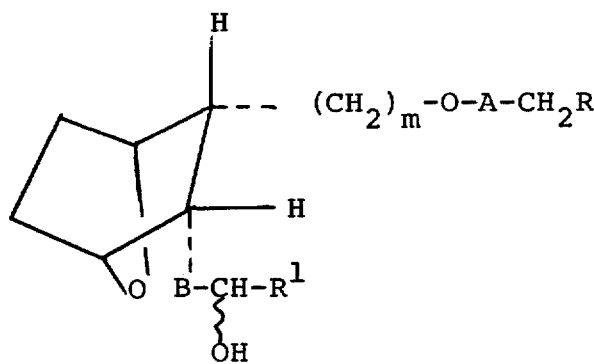

UNITED STATES PATENT AND TRADEMARK OFFICE
CERTIFICATE OF CORRECTION

PATENT NO. : 4,513,103
DATED : April 23, 1985
INVENTOR(S) : Jagabandhu Das, et al.

It is certified that error appears in the above—identified patent and that said Letters Patent is hereby corrected as shown below:

Column 12, structure IK should read

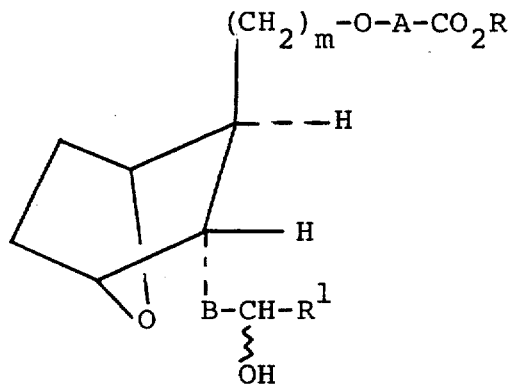

Column 13, line 1, "wavy ( )" should read --wavy ($\xi$)--.
Column 17, before line 29, insert --E.--.

Signed and Sealed this

Eighth Day of October 1985

[SEAL]

Attest:

DONALD J. QUIGG

Attesting Officer

Commissioner of Patents and Trademarks—Designate